(12) United States Patent
Shinoda et al.

(10) Patent No.: US 9,939,329 B2
(45) Date of Patent: Apr. 10, 2018

(54) DEVICE AND METHOD FOR THERMAL ANALYSIS

(71) Applicant: Netzsch-Gerätebau GmbH, Selb (DE)

(72) Inventors: Yoshio Shinoda, Tokyo (JP); Ryoichi Kinoshita, Shizuoka (JP)

(73) Assignee: Netzsch-Gerätebau GmbH, Selb (DE)

( * ) Notice: Subject to any disclaimer, the term of this patent is extended or adjusted under 35 U.S.C. 154(b) by 279 days.

(21) Appl. No.: 14/815,021

(22) Filed: Jul. 31, 2015

(65) Prior Publication Data

US 2016/0054181 A1    Feb. 25, 2016

(30) Foreign Application Priority Data

Aug. 22, 2014 (JP) .................. 2014-169762

(51) Int. Cl.
| | |
|---|---|
| *G01K 7/02* | (2006.01) |
| *G01N 25/48* | (2006.01) |
| *G01N 5/04* | (2006.01) |
| *G01K 13/00* | (2006.01) |

(52) U.S. Cl.
CPC .............. *G01K 7/02* (2013.01); *G01K 13/00* (2013.01); *G01N 5/04* (2013.01); *G01N 25/4833* (2013.01); *G01N 25/4866* (2013.01)

(58) Field of Classification Search
CPC ..................................... G01N 25/486
See application file for complete search history.

(56) References Cited

U.S. PATENT DOCUMENTS 7,470,057 B2 * 12/2008 Danley ................. G01N 25/18
                                                            374/12
8,042,992 B2 * 10/2011 Wijffels .............. G01N 25/482
                                                            374/12

FOREIGN PATENT DOCUMENTS

| EP | 0405153 B1 | 3/1994 |
| JP | 04299242 A * | 10/1992 |
| JP | 06213841 A * | 8/1994 |
| JP | 06229899 A * | 8/1994 |
| JP | 3127043 B2 | 1/2001 |
| JP | 3241427 B2 | 12/2001 |

* cited by examiner

*Primary Examiner* — Clayton E Laballe
*Assistant Examiner* — Leon W. Rhodes, Jr.
(74) *Attorney, Agent, or Firm* — Whitmyer IP Group LLC

(57) ABSTRACT

A device for thermal analysis including: a pair of sample container assembly sets, having a sample container and a heat sink connected using a predetermined thermal resistance; a heating unit for equally heating the pair of sample container assembly sets; a temperature control for the heating unit; a weight measurement unit measuring difference between a sample and a reference material; while the heating unit is changed.

10 Claims, 10 Drawing Sheets

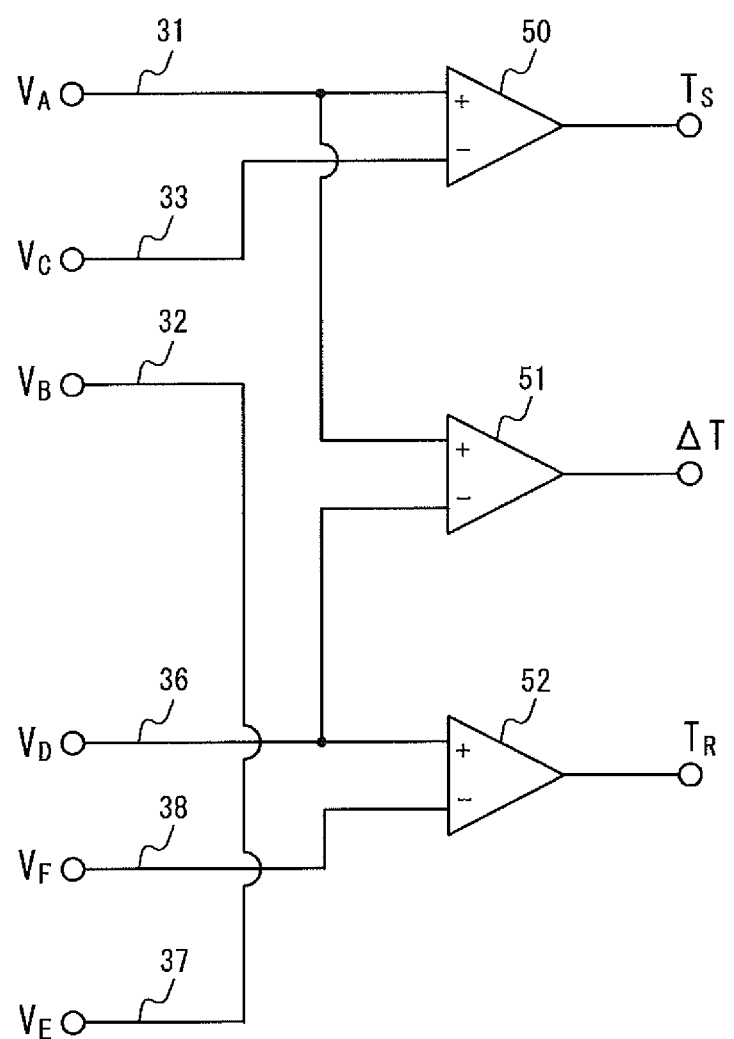

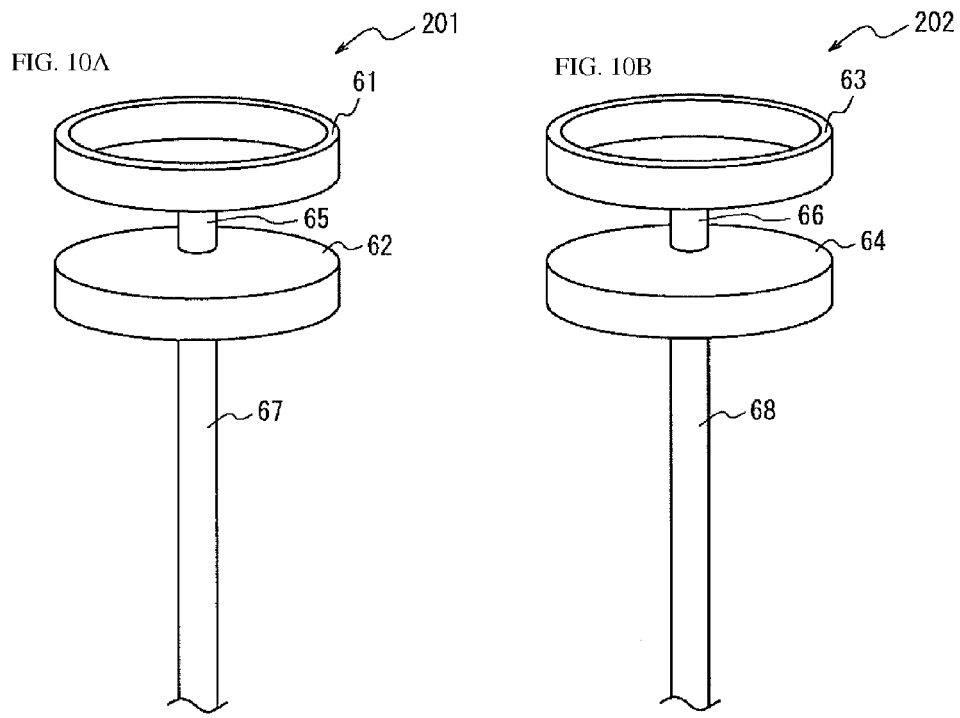
FIG. 10A
FIG. 10B
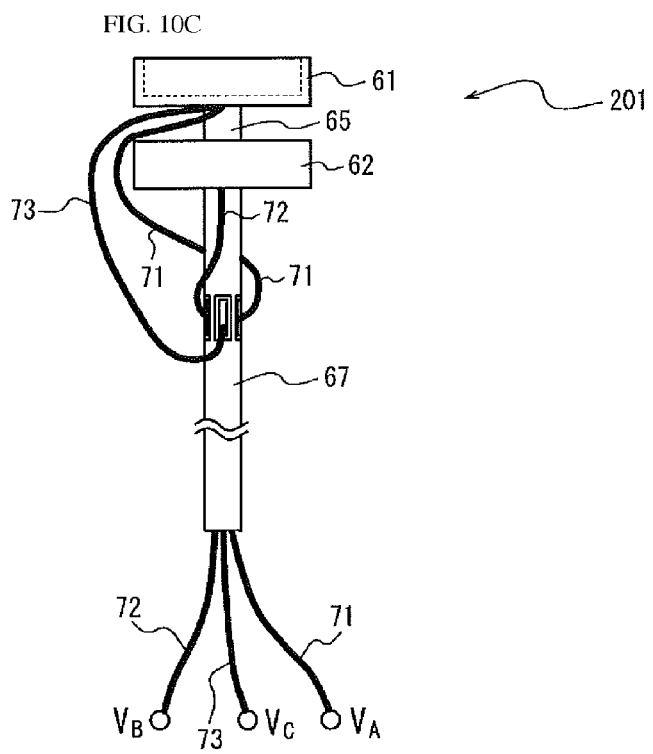
FIG. 10C

DEVICE AND METHOD FOR THERMAL ANALYSIS

FIELD OF THE INVENTION

The present invention relates to a device for analyzing weight change of a substance and generated and absorbed heat thereof with respect to temperature change, and a method therefor.

BACKGROUND OF THE INVENTION

Techniques are under development in which while changing the temperature of a sample, the weight change and the quantity of generated and absorbed heat are quantified thereby analyzing a thermal decomposition reaction of the sample and the like. Of those, thermogravimetry (hereinafter referred to as "TG") is a technique that is generally used for evaluating the heat resistance property of a sample and analyzing a heat decomposition reaction thereof, in which while the temperature of the sample is changed, the change in the weight of the sample is measured. This measurement can be performed using a thermogravimeter. Further, differential scanning calorimetry (hereinafter referred to as "DSC") is a technique for capturing the change in the temperature and the enthalpy caused by melting and phase transition of a sample (heat of fusion, heat of transition) and the like, thereby quantifying the temperature of reactions such as glass transition and hardening reaction; the heat of reaction; and the like. The DSC can be performed using a differential scanning calorimeter.

Similar techniques to the DSC includes differential thermal analysis (hereinafter referred to as "DTA") in which while the temperature of a sample is changed, the relative temperature change of a sample caused by phase transition, reactions, and the like with respect to a reference material is measured. In DSC, a heat sink is provided in terms of the device structure, and the generated and absorbed heat can be quantified by measuring the amount of heat moving between the sample and the heat sink. To the contrary, in DTA, although the transition temperature and the like of the sample can be measured, it is assumed to be difficult in terms of the structure, to measure generated and absorbed heat such as heat of transition.

Here, the principle of DSC will be described with reference to FIG. 11. FIG. 11 is a diagram showing the structure of a typical differential scanning calorimeter. A sample container loaded with a sample and a sample container loaded with a reference material are fixed to a heat sink through coupling members having a predetermined thermal resistance. The sample and the reference material are placed inside a furnace provided with a heat coil, and the temperature inside the furnace is controlled using a control unit not shown. A differential thermocouple is provided to measure the temperature difference $\Delta T$ between the temperature $T_S$ of the sample and the temperature $T_R$ of the reference material; the $\Delta T$ is calculated by dividing the voltage $V_{SR}$ at both ends of the differential thermocouple by the Seebeck coefficient inherent to the material of the thermocouple.

Provided that the temperature of the heat sink is $T_H$, the heat flow $dq_S/dt$, that is, the quantity of heat flowing from the heat sink to the sample per unit time is expressed by Equation (1).

[Equation 1]

$$\frac{dq_S}{dt} = \frac{1}{R}(T_H - T_S), \quad (1)$$

where R is a thermal resistance between the sample and the heat sink.

Similarly, the heat flow $dq_R/dt$ from the heat sink to the reference material is expressed by Equation (2).

[Equation 2]

$$\frac{dq_S}{dt} = \frac{1}{R}(T_H - T_S), \quad (2)$$

Accordingly, the relationship between $\Delta T$ and the difference $d\Delta q/dt$ between the heat flow from the heat sink to the reference material and the heat flow from the heat sink to the sample can be expressed by Equation (3), in which Equation (2) is subtracted from Equation (1).

[Equation 3]

$$\frac{d\Delta q}{dt} = \frac{dq_S}{dt} - \frac{dq_R}{dt} = \frac{1}{R}(T_R - T_S) = -\frac{1}{R}\Delta T \quad (3)$$

FIGS. 12(A) and 12(B) show the result of DSC during an endothermic reaction of the sample. The rise of the sample temperature $T_s$ is retarded during a period between the times $t_1$ and $t_2$ as shown in FIG. 12(A). As shown in FIG. 12(B), a peak of the difference $\Delta T_P$ between the temperatures of the sample and the reference material is observed in the same period. Note that the peak $\Delta T_P$ here is the difference between the temperature difference prior to the start of the endothermic reaction and the temperature at a time when the absorbed heat flow is maximized. Both sides of Equation (3) are integrated with respect to the period between the times $t_1$ and $t_2$ to obtain the following Equation (4).

[Equation 4]

$$\int_{t_1}^{t_2} \frac{d\Delta q}{dt} \cdot dt = -\frac{1}{R}\int_{t_1}^{t_2} \Delta T \cdot dt \quad (4)$$

The left side of Equation (4) is the amount of heat Q absorbed by the sample during the period between times $t_1$ and $t_2$, whereas $$\int_{t_1}^{t_2} \Delta T \cdot dt$$

in the right side is the area corresponding to the peak portion hatched in FIG. 12(B). Accordingly, the area of the peak portion is in proportion to the amount of heat Q absorbed by the sample.

Note that the coefficient R in Equation (3) that is used for determining the heat flow $d\Delta q/dt$ absorbed by the sample from the temperature difference $\Delta T$ can be calculated for example from the relationship between the area of the peak portion of the temperature difference $\Delta T$ obtained by performing a DSC measurement on a material which absorbs a known amount Q by melting and the amount of absorbed heat Q.

On the other hand, DTA does not involve a structure corresponding to the heat sink in DSC. Accordingly, although the transition temperature can be found from the peak of the absorbed heat, the temperature difference $\Delta T$ cannot be converted into the amount of absorbed heat Q.

In recent years, devices for simultaneously performing measurements using TG and DSC or DTA that have been described above. For example, such an analysis, in which while weight change resulted from solvent evaporation from a sample or thermal decomposition is captured by TG, the resultant endothermic/exothermic phenomenon is captured by DSC or DTA at the same time has become possible. These analyses and relevant devices are referred to as TG-DSC or TG-DTA. Such an analysis is also referred to as simultaneous thermal analysis (STA).

A typical structure of a TG-DSC is disclosed, for example, in EP 0405153 B (PTL 1). A device for thermal analysis disclosed in PTL 1 has sample holders capable of carrying a sample and a reference material, which holders are provided on the tip of one supporting rod extending upward from a balance mechanism. The sample holders include a sample container for carrying a sample and a sample container for carrying a reference material on a heat sink. Accordingly, a structure of DSC is employed in which the difference between the heat flow from a heat sink to a sample and the heat flow from the heat sink to a reference material is detected.

On the other hand, a typical structure of TG-DTA is disclosed, for example, in JP 3127043 B (PTL 2) and JP 3241427 B (PTL 3). PTL 2 discloses a thermogravity detector (TG-DTA) capable of measuring the weight difference and the temperature difference between a sample and a reference material on pans placed on vertical supporting rods of an upright (vertical) differential balance. DTA can be performed by measuring the temperature difference between the sample and the reference material; however, a heat sink for measuring the difference between the heat flow from the heat sink to the sample and the heat flow from the heat sink to the reference material is not provided. Thus, the TG-DTA does not have a structure of DSC.

PTL 3 discloses a device for thermal analysis, capable of measuring the weight difference and the temperature difference between a sample and a reference material placed on respective holders provided on the tip of two horizontally extending beams in a horizontal differential balance (TG-DTA). DTA can be performed by measuring the temperature difference between the sample and the reference material; however, a heat sink for measuring the difference between the heat flow from the heat sink to the sample and the heat flow from the heat sink to the reference material is not provided. Thus, the TG-DTA does not have a structure of DSC as with PTL 2.

PATENT LITERATURE

PTL 1: EP 0405153 B
PTL 2: JP 3127043 B
PTL 3: JP 3241427 B

SUMMARY OF INVENTION

Technical Problem

In TG-DSC described in PTL 1, the total weight of the sample holders connected to the supporting rod is measured; therefore, the buoyancy, convection flows, and the like of the case where the temperature is changed by heating the sample influence the measured weight value. Accordingly, in order to accurately measure the weight change of a sample, it is necessary that a measurement is first performed without placing the sample and a reference material (blank measurement), and the blank measurement data is subtracted after the sample measurement so as to cancel the effects of the buoyancy and convection flows. Thus, there has been a problem of complex measurement procedure.

Further, since both TG-DTAs described in PTL 2 and PTL 3 use a differential balance, the sample side and the reference material side are necessarily separated mechanistically. Therefore, a heat sink for measuring the difference between the heat flow from the heat sink to a sample and the heat flow from the heat sink to a reference material cannot be provided. Thus, it is difficult to achieve a structure of a DSC, which has been a problem.

An object of the present invention made in view of those circumstances is to provide a device for thermal analysis capable of highly accurate TG-DSC measurement without a complex measurement procedure.

Solution to Problem

In order to solve the above problems, a device for thermal analysis according to the present invention comprises:

a pair of sample container assembly sets including a first sample container assembly and a second sample container assembly, in each of which a sample container and a heat sink are connected using a member having a predetermined thermal resistance;

a heating unit for equally heating the pair of sample container assembly sets;

a temperature control unit for controlling the temperature of the heating unit;

a weight measurement unit for measuring the weight difference between a sample placed on the sample container of the first sample container assembly and a reference material placed on the sample container of the second sample container assembly; and a temperature measurement unit for measuring the temperature difference between the sample and the reference material, and while the temperature of the heating unit is changed using the temperature control unit, the weight difference and the temperature difference are measured.

Preferably, the temperature measurement unit comprises:

thermocouple elements made of first metal, connected to the sample containers and the heat sinks; and thermocouple elements made of second metal, connected to the sample containers, and the member having the thermal resistance is a member made of the second metal.

Preferably, the first metal is platinum, and the second metal is a platinum rhodium alloy.

Further, it is preferable that the first metal is a platinum rhodium alloy, and the second metal is platinum.

Preferably, the heating unit has a cylindrical shape, and the sample container of the first sample container assembly and the sample container of the second sample container assembly are placed at symmetrical positions with respect to the center axis of the cylindrical shape.

Preferably, the heating unit has a cylindrical shape, and the heat sink of the first sample container assembly and the heat sink of the second sample container assembly are placed at symmetrical positions with respect to the center axis of the cylindrical shape.

Preferably, the sample containers and the heat sinks are all placed equidistant from the center axis of the cylindrical shape.

Preferably, the heat sinks are placed at the same height as the sample containers.

Preferably, the sample container of the first sample container assembly is placed coaxially with the center axis of the heat sink of the first sample container assembly, and the sample container of the second sample container assembly is placed coaxially with the center axis of the heat sink of the second sample container assembly.

Preferably, the heat sinks have a heat capacity equal to or more than twice that of the sample containers.

Preferably, the weight measurement unit is a balance configured to measure the weight difference between the sample container assemblies.

Further, in order to solve the above problems, a method for thermal analysis according to the present invention uses a device for thermal analysis including:

a pair of sample container assembly sets including a first sample container assembly and a second sample container assembly, in each of which a sample container and a heat sink are connected using a member having a predetermined thermal resistance; and a heating unit for equally heating the first sample container assembly and the second sample container assembly, and the method comprises the steps of:

while changing the temperature of the heating unit, measuring the weight difference between a sample in the sample container of the first sample container assembly and a reference material in the sample container of the second sample container assembly; and at the same time as the measurement of the weight difference, measuring the temperature difference between the sample and the reference material.

Advantageous Effect of Invention

Using a device for thermal analysis according to the present invention, highly accurate TG-DSC measurement can be realized without a complex measurement procedure.

BRIEF DESCRIPTION OF DRAWINGS

FIG. 5 is a schematic of a temperature measurement unit included in a device for thermal analysis according to embodiments of the present invention.

FIGS. 10(A) to 10(C) are diagrams showing a sample container assembly and thermocouple elements which compose a device for thermal analysis according to Embodiment 2 of the present invention.

DETAILED DESCRIPTION OF THE INVENTION

Embodiments of the present invention will now be described in detail with reference to the drawings.

(Embodiment 1)

Figure 1:
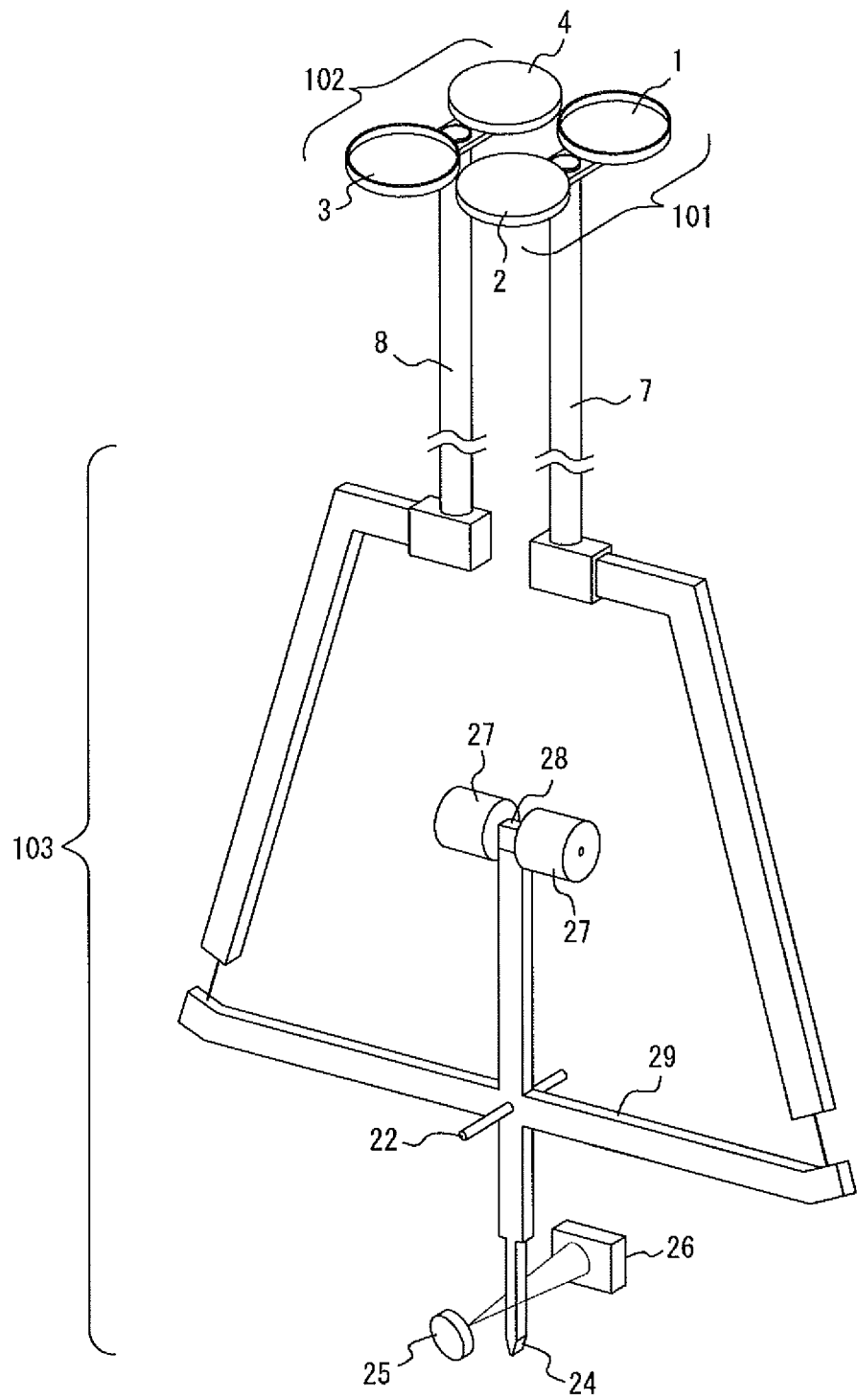
FIG. 1 is a diagram showing the structure of a mechanism part of a device for thermal analysis according to Embodiment 1 of the present invention.

FIG. 1 is a diagram showing the structure of a mechanism part of a device for thermal analysis according to Embodiment 1 of the present invention. A device for thermal analysis 100 according to this embodiment includes a sample container assembly 101 for carrying a sample, a sample container assembly 102 for carrying a reference material, and a balance 103 for measuring the weight difference between the sample and the reference material. The device for thermal analysis 100 further includes a heating furnace 20, a balance control unit 200, a temperature measurement unit 300, and a temperature control unit 400, which are to be described later.

First, the sample container assemblies 101, 102 are described.

Figure 2:
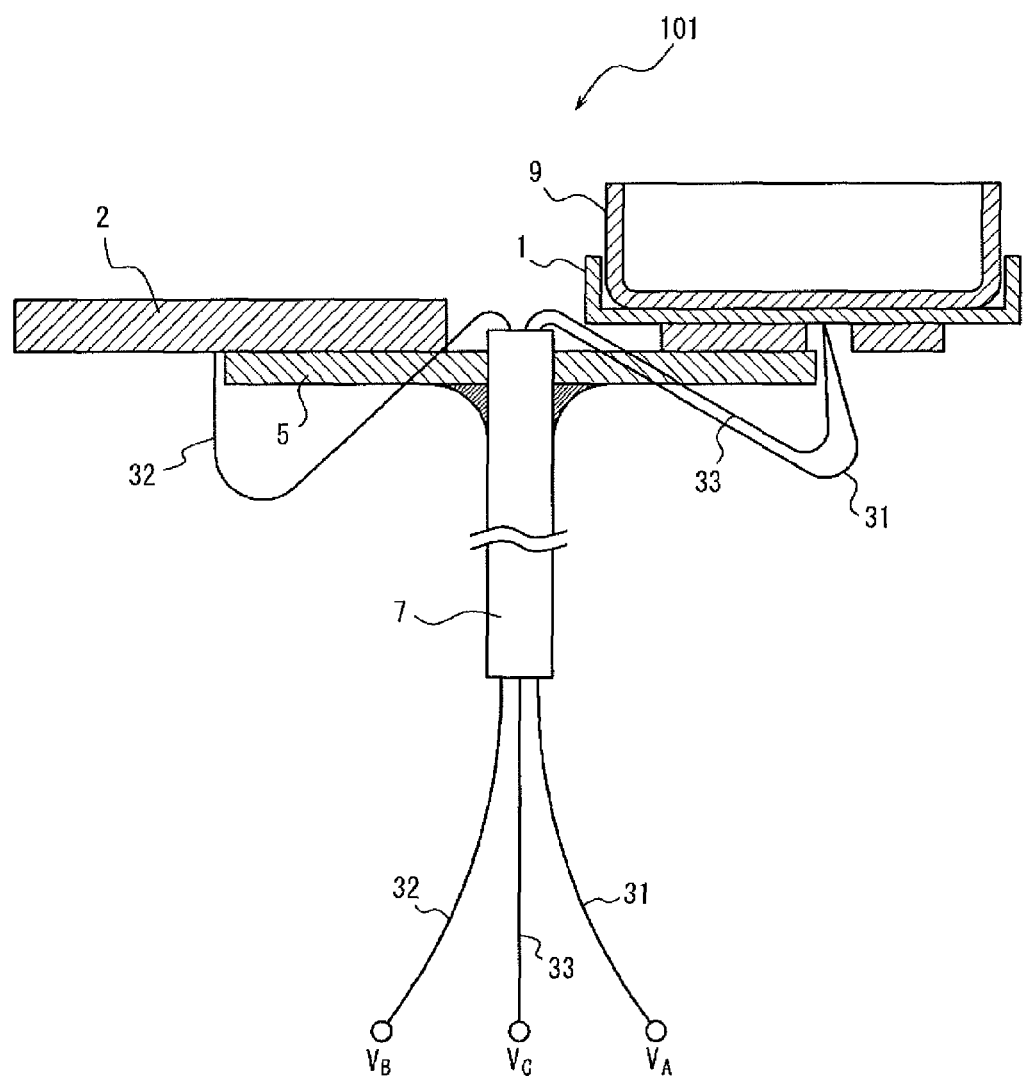
FIG. 2 is a diagram showing a cross section of a sample container assembly and thermocouple elements which compose a device for thermal analysis according to Embodiment 1 of the present invention.

FIG. 2 is a diagram showing a cross section of a sample container assembly 101 and thermocouple elements which compose the device for thermal analysis 100 of this embodiment. The sample container assembly 101 includes a container holder 1, a sample container 9 placed on the container holder 1, a heat sink 2 having a predetermined heat capacity, a coupling member 5 for coupling the container holder 1 and the heat sink 2, and a beam 7 having three insulation holes. Further, FIG. 2 shows a thermocouple element A 31 and a thermocouple element B 33 each of which is provided to have an end connected to the bottom of the container holder 1, with a thermocouple element A 32 which is provided to have an end connected to the bottom of the heat sink 2. The container holder 1, the coupling member 5, and the heat sink 2 can be coupled for example by welding. Similarly, each of the thermocouple elements A 31, 32 and the thermocouple element B 33 can be connected to the bottom of the container holder 1 or the heat sink 2 by welding. Further, the coupling member 5 and the beam 7 can be fastened for example at the underside of the coupling member 5 using an alumina-based adhesive. Note that both the sample container 9 and the container holder 1 of this embodiment are "sample containers" composing a device for thermal analysis of the claimed invention. The same applies to a sample container 10 and a container holder 3 to be described later.

The container holder 1 is a holder for carrying the sample container 9 having a circular shape in plan view. The container holder 1 has a rather recessed part having a slightly larger diameter than the outer diameter of the sample container 9, and the sample container 9 can be fitted into the recessed part.

The heat sink 2 has a circular shape having almost the same diameter as the container holder 1. The heat sink 2 is desirably maintained at the same temperature as the internal temperature of the heating furnace 20 without being influenced by temperature change of the sample and the like. Therefore, the heat capacity of the heat sink 2 is preferably more than twice the sum of the heat capacities of the sample container 9 and the container holder 1.

The coupling member 5 is a plate member having a predetermined heat capacity and having a rectangular shape in plan view. In this embodiment, the material of the coupling member 5 can be, for example, platinum which is the material of the container holders 1, 3. The thermal resistance of the coupling member 5 determines the thermal resistance R in Equation (3).

The beam 7 is a heat-resistant member having a rod-like external shape. The beam 7 constitutes a three-hole insulating tube having three insulation holes. For the material of the beam 7, for example, alumina can be used. The beam 7 is disposed to extend in the vertical direction and allows the sample and the like to be placed on the differential balance 103 and allows thermocouple elements for measuring the temperature of the sample and the like to be routed through the insulation holes.

The sample container 9 is a container for carrying a sample to be measured and is positioned by being fitted into the recessed part of the container holder 1. The material of the sample container 9 can be, for example, alumina considering the measurement temperature conditions and the like.

In this embodiment, for example, the material of the container holder 1, the heat sink 2, the coupling member 5, and the thermocouple element B 33 can be platinum (Pt), whereas the material of the thermocouple elements A 31, 32 can be a platinum rhodium alloy (PtRh). Using these materials as components, the connection between the thermocouple element A 31 and the thermocouple element A 32 forms a PtRh—Pt—PtRh joint. With this structure, the temperature difference between one PtRh—Pt joint and the other PtRh—Pt joint can be measured. Further, this temperature difference is the temperature difference between the container holder 1 and the heat sink 2 of the sample container assembly 101. Note that this thermocouple composed of platinum and a platinum rhodium alloy is characteristically capable of measuring high temperatures of 1500° C. or more although the change in thermoelectromotive force, or the Seebeck coefficient is small.

Further, the temperature difference between one PtRh—Pt joint and the other PtRh—Pt joint in the above PtRh—Pt—PtRh joint can be measured as a voltage difference $(V_A-V_B)$ between the thermocouple element A 31 and the thermocouple element A 32 as shown in FIG. 2.

In this embodiment, since the sample container 9 is fitted into the recessed part of the container holder 1, the temperature difference between the sample container 9 and the heat sink 2 is considered to be approximate to the temperature difference between the container holder 1 and the heat sink 2, measured using the above PtRh—Pt—PtRh joint.

Further, in FIG. 2, the thermocouple element A 31 and the thermocouple element B 33 form the PtRh—Pt joint at the position of the container holder 1. Accordingly, the temperature of the container holder 1 can be determined by measuring the voltage difference $(V_A-V_C)$ between the thermocouple element A 31 and the thermocouple element B 33. The temperature of the sample container 9 and the sample is considered to be approximate to the temperature of the container holder 1.

Although not shown in FIG. 2, as with the sample container assembly 101, the sample container assembly 102 includes a container holder 3, a sample container 10 placed on the container holder 3, a heat sink 4 having a predetermined heat capacity, a coupling member 6 for coupling the container holder 3 and the heat sink 4, a beam 8 having three insulation holes, a thermocouple element A 36 and a thermocouple element B 38, one end of each of which is connected to the bottom of the container holder 3, and a thermocouple element A 37 provided to have an end connected to the bottom of the heat sink 4. For the members composing the sample container assembly 102, components having the same shape and the same material as the members of the sample container assembly 101 are used.

Figure 3:
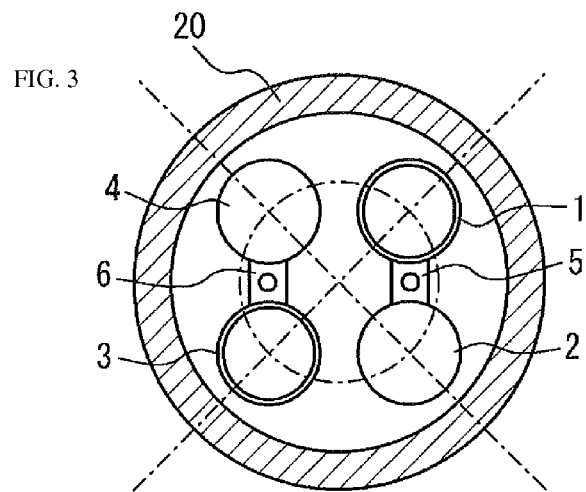
FIG. 3 is a plan view of sample container assemblies composing a device for thermal analysis according to Embodiment 1 of the present invention.

FIG. 3 is a plan view showing sample container assemblies 101, 102 and a heating furnace 20. The heating furnace 20 has, for example, a cylindrical shape, and the container holders 1 and 3 can be placed at axially symmetric positions with respect to the center axis of the heating furnace 20. The heat sinks 2 and 4 can be similarly placed at axially symmetric positions with respect to the center axis of the heating furnace 20. In that case, the container holders 1 and 3 and the heat sinks 2 and 4 are desirably placed equidistant from the center axis of the heating furnace 20. Note that although the sample containers 9, 10 are omitted in FIG. 3, the sample containers 9, 10 having a circular shape in plan view are fitted into the container holders 1, 3 which also have a circular shape. Thus, the sample containers 9, 10 are positioned coaxially with the center axis of the container holders 1, 3. Accordingly, the sample containers 9, 10 are also placed at axially symmetric positions with respect to the center axis of the heating furnace 20. Further, the sample containers 9 and 10 and the heat sinks 2 and 4 are all placed equidistant from the center axis of the heating furnace 20.

Next, the balance 103 is described.

As shown in FIG. 1, the balance 103 is configured such that a balance lever 29 is provided to be swingable around a main shaft 22 in accordance with the weight difference between the sample placed on the sample container assembly 101 and a reference material placed on the sample container assembly 102. In this embodiment, the balance 103 constitutes an electronic balance using electromagnetic force. The balance 103 detects a displacement of a shutter 24 caused when the balance lever 29 swings, using a light emitting device 25 and a light receiving device 26. Here, the light emitting device 25 can be, for example, a light emitting diode device which emits infrared light. The light receiving device 26 can be, for example, a device in which two phototransistors are arranged in the direction of the displacement of the shutter 24. The balance control unit 200 performs control such that the shutter 24 always stays at a predetermined position by applying driving force to a magnet 28 coupled to the balance lever 29 by supplying current to a driving coil 27 in accordance with the amount of displacement of the shutter 24, detected by the light receiving device 26.

Figure 4:
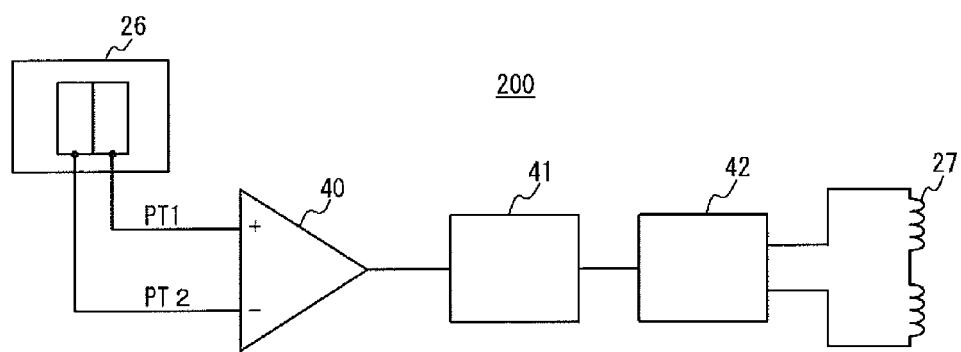
FIG. 4 is a block diagram of a balance control unit included in a device for thermal analysis according to embodiments of the present invention.

FIG. 4 is a block diagram showing the configuration of the balance control unit 200. Detection signals PT1, PT2 from the light receiving device 26 are input to a differential amplifier 40. A differential output (PT1−PT2) from the differential amplifier 40 is phase compensated by a phase compensator 41 and then converted into a current signal in a current driver 42 to be supplied to the driving coil 27.

The balance 103 detects a low frequency component of the current signal supplied to the driving coil 27 by the balance control unit 200 as the weight difference between a sample and a reference material.

As mentioned above, since the sample containers 9, 10 are placed at axially symmetric positions in the cylindrical heating furnace 20, the effects of the buoyancy and convection flows caused due to heating on gravity measurement can be canceled.

Next, the temperature measurement unit 300 is described.

FIG. 5 is a block diagram showing the configuration of the temperature measurement unit 300. The voltages $V_A$, $V_B$, $V_C$ of the thermocouple element A 31, the thermocouple element A 32, and the thermocouple element B 33 of the sample container assembly 101 are input to the temperature measurement unit 300. Similarly, the voltages $V_D$, $V_E$, $V_F$ of the thermocouple element A 36, the thermocouple element A 37, and the thermocouple element B 38 of the sample container assembly 102 are input thereto.

As described above, the voltage difference $(V_A-V_B)$ between the voltage $V_A$ of the thermocouple element A 31 and the voltage $V_B$ of the thermocouple element A 32 shows the temperature difference between the container holder 1 and the heat sink 2 of the sample container assembly 101. Similarly, the voltage difference $(V_D-V_E)$ between the voltage $V_D$ of the thermocouple element A 36 and the voltage $V_E$ of the thermocouple element A 37 shows the temperature difference between the container holder 3 and the heat sink 4 of the sample container assembly 102. In the temperature measurement unit 300 in FIG. 5, a circuit is configured such that the thermocouple element A 32 and the thermocouple element A 37 are short circuited ($V_B=V_E$ holds), and the difference $(V_A-V_D)$ between $(V_A-V_B)$ and $(V_D-V_E)$ above can be directly detected. Specifically, the voltage $V_A$ of the thermocouple element A 31 and the voltage $V_D$ of the thermocouple element A 36 are input to a differential amplifier 51, such that the voltage difference $(V_A-V_D)$ can be measured as an output voltage of the differential amplifier 51. Thus, the temperature difference between the container holder 1 and the container holder 3, that is, the temperature difference ΔT between the sample and the reference material can be directly detected as an output voltage of the differential amplifier 51.

Further, as mentioned above, the temperature of the container holder 1 can be determined by measuring the voltage difference (VA–VC) between the thermocouple element A 31 and the thermocouple element B 33. Here, the sample container 9 is made of alumina that has a high thermal conductivity, and the sample container 9 is fitted into the recessed part of the container holder 1; thus, the temperature of the measured container holder 1 can be regarded as the temperature $T_S$ of the sample placed in the sample container 9. The temperature measurement unit 300 is configured such that the differential amplifier 50 outputs $(V_A-V_C)$ corresponding to $T_S$. Similarly, it is configured such that the differential amplifier 52 outputs $(V_D-V_F)$ corresponding to $T_R$.

Note that for the conversion from an output voltage difference to a temperature, for example, DSC measurement is performed on a material having a known transition temperature, and the compensation of the converted temperature value (temperature calibration) can be performed based on the output voltage difference and the transition temperature of the material.

Figure 6A:
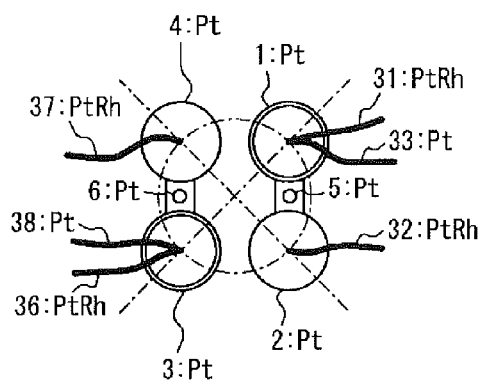
FIGS. 6(A) to 6(D) are diagrams showing combinations of materials of sample container assemblies and thermocouple elements which compose a device for thermal analysis according to Embodiment 1 of the present invention.

FIGS. 6(A) to 6(D) are diagrams showing variations of material choices of the container holders 1, 3, heat sinks 2, 4, coupling members 5, 6, thermocouple elements A 31, 32, 36, 37, and thermocouple elements B 33, 38. Note that the sample containers 9, 10 are omitted in FIGS. 6(A) to 6(D). FIG. 6(A) is an example of a material choice in this embodiment described above, in which a PtRh—Pt joint is formed at the boundary between the thermocouple elements A 31, 36 and the container holders 1, 3, and at the boundaries between the heat sinks 2, 4 and the thermocouple elements A 32, 37.

Figure 6B:
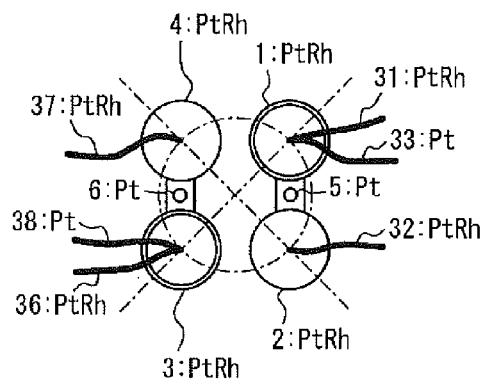

Meanwhile, FIG. 6(B) is an example of changing the material of the container holders 1, 3 and the heat sinks 2, 4 from Pt in FIG. 6(A) to PtRh. In this structure, a PtRh—Pt joint is formed at the boundary between the container holders 1, 3 and the coupling members 5, 6, and at the boundary between the coupling members 5, 6 and the heat sinks 2, 4, so that the temperature difference and the temperature can be measured at those boundaries.

Figure 6C:
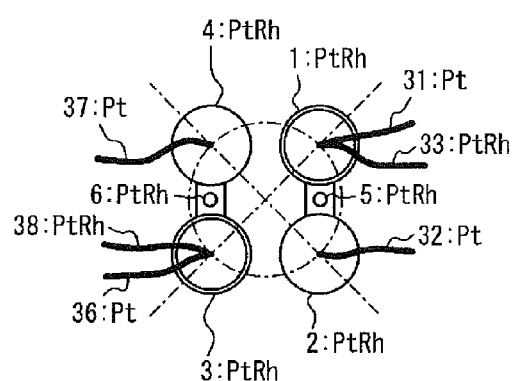

FIG. 6(C) is an example of a structure in which Pt and PtRh in FIG. 6(A) are exchanged. Also in this example, a PtRh—Pt joint is formed at the same locations as in FIG. 6(A), so that the measurement similar to the structure of FIG. 6(A) can be performed.

Figure 6D:
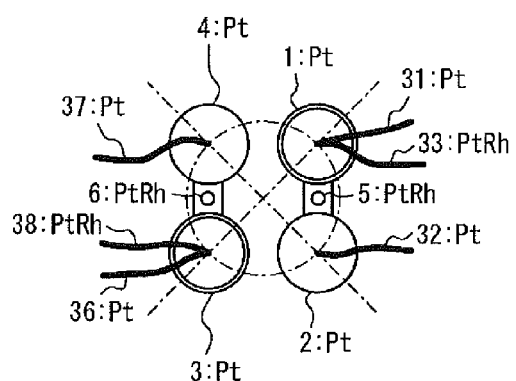

FIG. 6(D) is an example of a structure in which Pt and PtRh in FIG. 6(B) are exchanged. In this example, a PtRh—Pt joint is formed at the same locations as in FIG. 6(B), so that the measurement similar to the structure of FIG. 6(B) can be performed.

Next, the structure of the heating furnace 20 is described.

Figure 7:
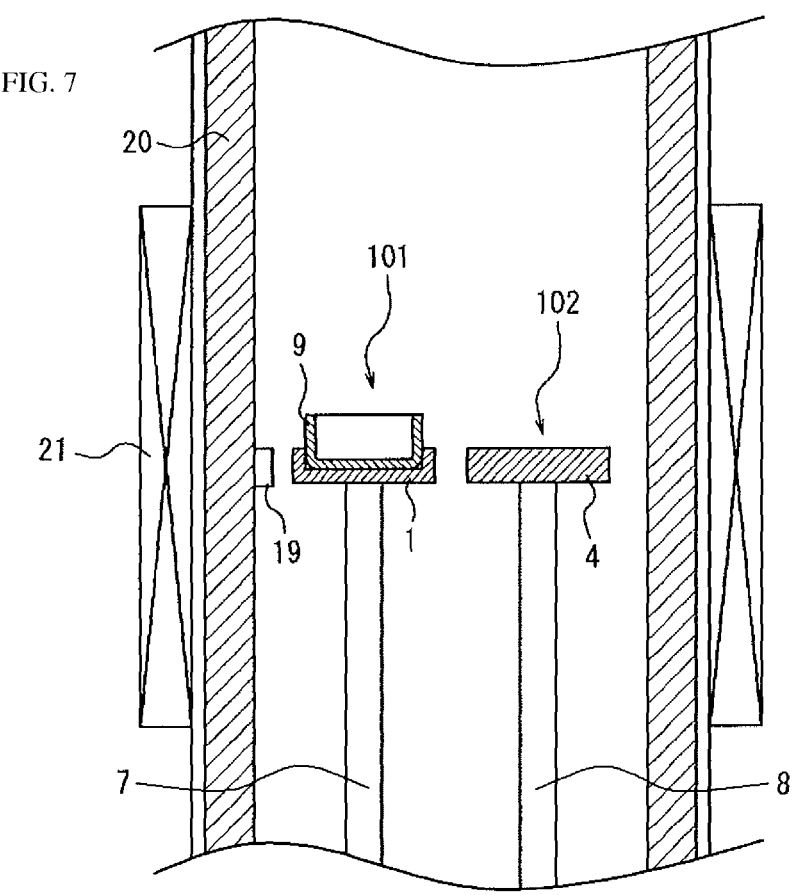
FIG. 7 is a diagram showing a sample container assembly included in a device for thermal analysis according to Embodiment 1 of the present invention with a cross section of a heating furnace.

FIG. 7 is a diagram showing the sample container assemblies 101, 102 being incorporated in the heating furnace 20. As mentioned above, the heating furnace 20 has a cylindrical shape, and the heat coil 21 is helically wound around the heating furnace 20. The heat coil 21 is wound up and down for the same distance from the height of the bottom of the sample containers 9, 10 and the heat sinks 2, 4. With this structure, a temperature distribution is formed in the heating furnace 20 such that the temperature is maximized at the positions at the height of the sample containers 9, 10 and the heat sinks 2, 4. Further, since the sample containers 9, 10 and the heat sinks 2, 4 are equidistant from the center axis of the heating furnace 20 in the radial direction, they are equidistant also from the cylinder wall surface of the heating furnace 20. Therefore, the sample containers 9, 10 and the heat sinks 2, 4 are equally heated by the heating furnace 20. A furnace temperature sensor 19 for measuring the temperature of the heating furnace 20 is placed at a position on the inner face of the heating furnace 20 at the same height as the sample containers 9, 10. For example, a thermocouple having a PtRh—Pt joint can be used as the furnace temperature sensor 19.

Note that for the material of the heat coil 21, for example, a platinum alloy can be used in consideration of the measurement temperature range.

Figure 8:
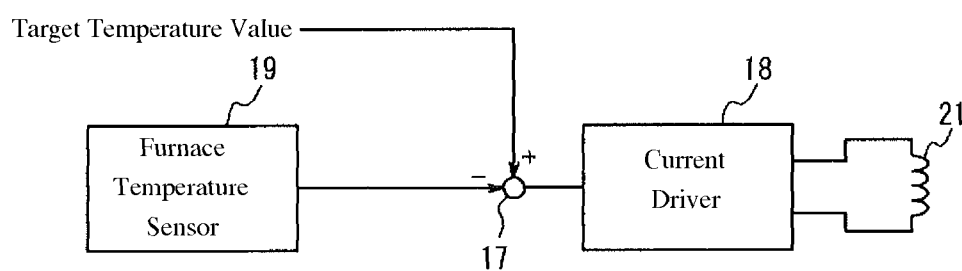
FIG. 8 is a block diagram of a temperature control unit for controlling the temperature of a heating furnace included in a device for thermal analysis according to embodiments of the present invention.

The temperature inside the heating furnace is controlled by the temperature control unit 400 shown in FIG. 8. The temperature control unit 400 drives a current driver 18 based on the difference between the target temperature value and the furnace temperature from the furnace temperature sensor 19 calculated in a comparator 17 to supply current to the heat coil 21.

Next, an example of performing thermal analysis of a material using a device for thermal analysis 100 according to this embodiment is described.

Figure 9:
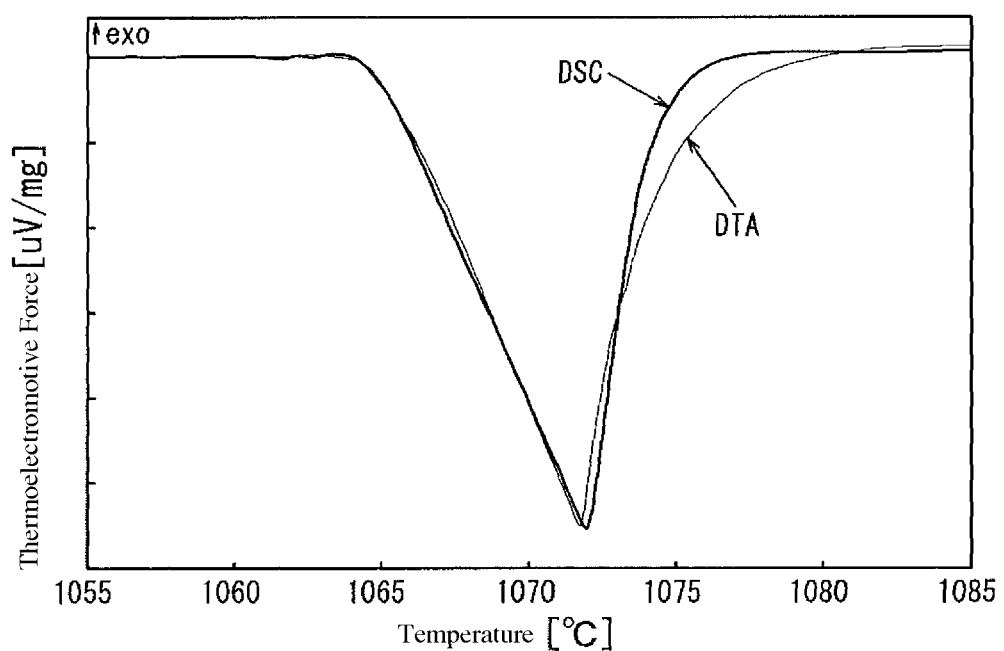
FIG. 9 is a diagram showing the comparison of signals at the endothermic peak during melting of gold between a device for thermal analysis according to Embodiment 1 of the present invention and a conventional TG-DTA.
Figure 11:
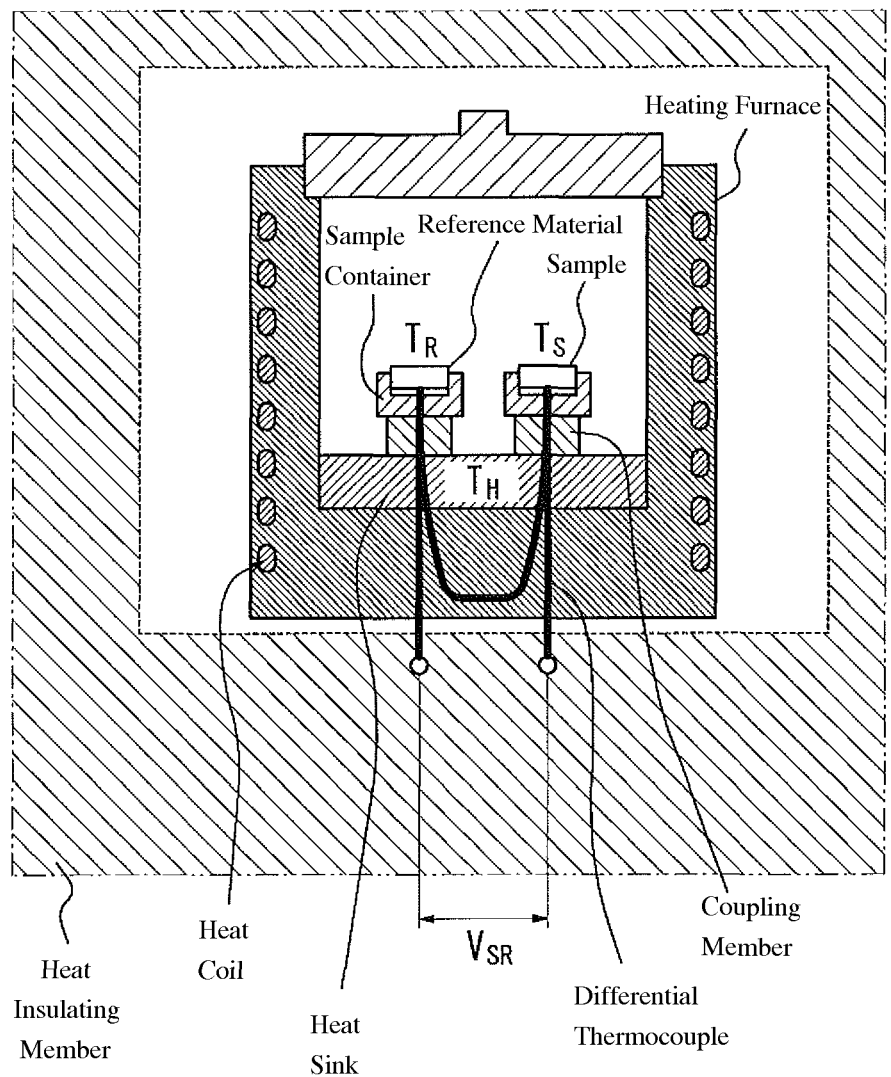
FIG. 11 is a diagram showing an example of the structure of a conventional DSC.
Figure 12A:
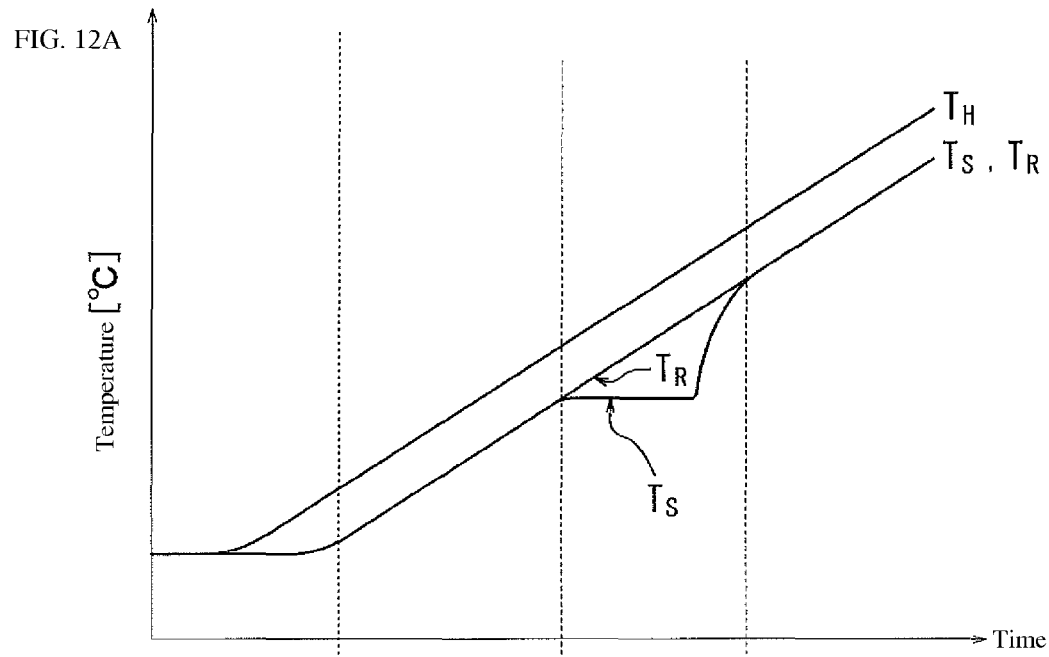
FIGS. 12(A) and 12(B) are graphs showing the relationship between the time and the temperature difference ΔT obtained by conventional DSC.
Figure 12B:
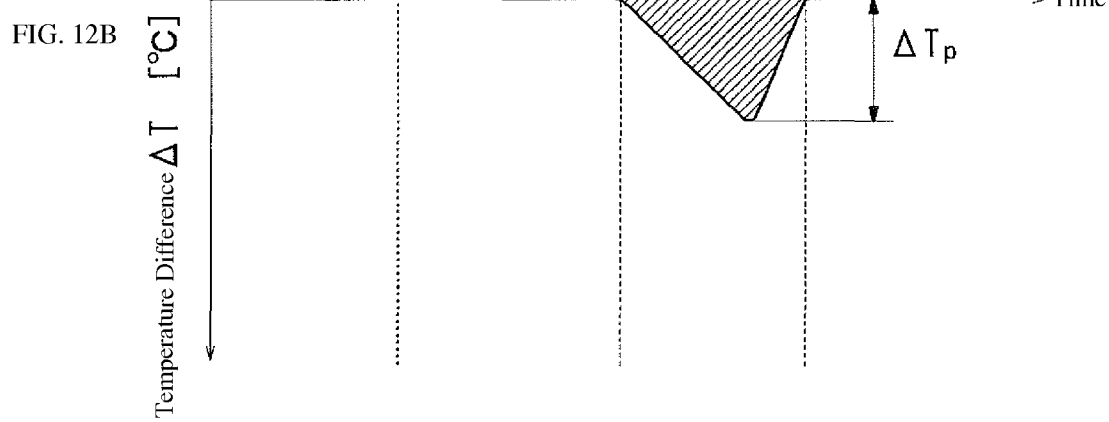

FIG. 9 is a diagram showing an endothermic reaction during the melting of a sample in the case where the temperature of the heating furnace 20 is raised at a constant rate by changing the target temperature value by the temperature control unit 400. The sample used in this example is gold. The horizontal axis of the graph represents the sample temperature $T_S$ measured by the thermocouple elements A 31, 33, whereas the vertical axis represents the thermoelectromotive force of the thermocouple, corresponding to the temperature difference ΔT between the sample (gold) and the reference material, which is converted into a value per unit sample mass (mg). FIG. 9 is shown such that the plus direction on the vertical axis means exothermic reaction of the sample.

The temperature difference ΔT between the sample and the reference material can be converted to the difference $d\Delta q/dt$ between the heat flow from the heat sink to the reference material and the heat flow from the heat sink to the sample by Equation (3). Here, the thermal resistance R between the sample and the reference material, used in Equation (3) can be calculated in advance using a known material as described above.

FIG. 9 shows the thermoelectromotive force (denoted as DSC in FIG. 9) obtained by the device for thermal analysis 100 according to this embodiment and data obtained by the thermogravity detector described in PTL 2 (denoted as DTA in FIG. 9). The thermogravity detector of PTL 2 has a structure of a TG-DTA and is not capable of quantifying the heat absorbed by the sample, using the thermoelectromotive force. Here, the peak value obtained from the data obtained by the thermogravity detector of PTL 2 is plotted to conform to the values obtained by the device for thermal analysis 100 of this embodiment. As can be seen from a comparison between both of them, in the device for thermal analysis 100 according to this embodiment, the temperature of the sample side recovers sooner after heat absorption than the thermogravity detector of PTL 2, so that the time constant is smaller. This is because the device for thermal analysis 100 according to this embodiment has a structure of a DSC, in which the sample container 9 and the heat sink 2 are connected with low thermal resistance, which leads to constant heat supply, and the sample container 9 returns to the base line due to heat inflow from the heat sink 2 immediately after the endothermic reaction ends. On the other hand, in the thermogravity detector of PTL 2, due to the absence of the connection between the sample container and the heat sink, the recovery of the temperature of the sample container after the endothermic reaction is likely to retard. Thus, the device for thermal analysis 100 of this embodiment has a structure of a DSC, in which the sample container 9 is connected to the heat sink 2, which makes it possible to accurately measure the transition phenomenon of the sample during the reaction.

In this embodiment, the heating furnace 20 is configured to have a cylindrical shape considering, for example the ease of winding the heat coil 21; however, the present invention is not limited to this embodiment. For example, the heating furnace 20 may be configured to have another shape such as of a rectangular prism shape. The same applies to the shape of the sample containers 9, 10, the container holders 1, 3, and the heat sinks 2, 4.

Further, in this embodiment, platinum and platinum rhodium are used as the materials of the thermocouple elements A 31, 32, 36, 37, thermocouple elements B 33, 38, container holders 1, 3, and heat sinks 2, 4; however, the present invention is not limited to this embodiment. The thermocouple elements may be made using, for example, tungsten and a tungsten-rhenium alloy; iridium and a iridium-rhodium alloy; or the like. The end of the thermocouple element A 31 on the container holder 1 side and the end of thermocouple element A 32 on the heat sink 2 side are connected in addition by a thermocouple element B, which allows the thermocouple elements to be made of a different metal from the container holders 1, 3 and the heat sinks 2, 4.

In this embodiment, a platinum alloy is used as the material of the heat coil 21; however, the present invention is not limited to this embodiment. Alternatively, another heat-resistant material such as molybdenum or silicon carbide (SiC) may be used.

As described above, according to this embodiment, the device is configured such that while the structure of a DSC is maintained, the weight difference between a sample and a reference material can be measured, thereby measuring the weight change of the sample at the same time as the measurement of the quantity of heat generated and absorbed by the sample. More specifically, the device is configured such that the sample container 9 on the sample side and the sample container 10 on the reference material side are mechanistically separated, and the weight difference between them can be measured by the differential balance 103. On the other hand, the sample containers 9, 10 provided with the heat sinks 2, 4 are provided axially symmetric in the heating furnace 20, so that the heat generated and absorbed by the sample can be accurately measured. Thus, according to the above embodiment, DSC measurement can be performed while achieving the benefits of differential thermogravimeters.

Further, according to this embodiment, a PtRh—Pt—PtRh joint is formed by two thermocouple elements A 31, 32, a container holder 1, a coupling member 5, and a heat sink 2; thus, the temperature difference between the sample and the heat sink 2 can be measured with a simple structure.

According to this embodiment, platinum rhodium is used for the thermocouple elements A, and platinum is used for the thermocouple element B, so that TG-DSC measurement can be performed up to the sample temperature of 1500° C. or more.

According to this embodiment, the sample containers 9 and 10 are placed at symmetrical positions with respect to the center axis of the cylindrical heating furnace 20, and the heat sinks 2 and 4 are also placed at symmetrical positions with respect to the center axis of the cylindrical heating furnace 20. Further, the sample containers 9, 10 and the heat sinks 2, 4 are placed equidistant from the center axis of the heating furnace 20. Further, the sample containers 9, 10 and the heat sinks 2, 4 are all placed at the same height. With this structure, the sample containers 9, 10 and the heat sinks 2, 4 are equally heated in the heating furnace 20, so that in weight difference measurements, the effects of the buoyancy and convection flows can be surely cancelled and in addition, more accurate DSC measurement can be performed.

Next, a second embodiment of the present invention will now be described in detail with reference to the drawings.

(Embodiment 2)

FIGS. 10(A) to 10(C) are diagrams showing sample container assemblies 201 and 202 and thermocouple elements that compose a device for thermal analysis 500 according to Embodiment 2 of the present invention. The sample container assembly 201 shown in FIG. 10(A) includes a container holder 61, a heat sink 62 having a predetermined heat capacity, a coupling member 65 for coupling the container holder 61 and the heat sink 62, and a beam 67 having three insulation holes. Note that a sample container 69 to be mounted on the container holder 61 and a sample are not shown. The container holder 61 and the heat sink 62 both have a circular shape in plan view, and the container holder 61 is placed above the heat sink 62, coaxially with the center axis of the heat sink 62. For example, platinum can be used as the material of the container holder 61, the heat sink 62, and the coupling member 65, which can be connected by welding or the like. The beam 67 can be connected, for example, to the rear surface of the heat sink 62 using an alumina-based adhesive.

FIG. 10(B) shows the sample container assembly 202 for carrying a reference material. As with the sample container assembly 201, the sample container assembly 202 includes a container holder 63, a heat sink 64 having a predetermined heat capacity, a coupling member 66 for coupling the container holder 63 and the heat sink 64, and a beam 68 having three insulation holes. Note that a sample container 70 to be mounted on the container holder 63 and a reference sample are not shown. The sample container assembly 202 has the same structure as the sample container assembly 201, except that the reference material is loaded instead of a sample, so that further explanation is omitted here.

FIG. 10(C) is a diagram showing a state where thermocouple elements A 71, 72 and a thermocouple element B 73 for temperature measurement are connected to the sample container assembly 201. One end of each of the thermocouple element A 71 and the thermocouple element B 73 is connected to the bottom of the container holder 61, and the other end thereof is routed downward from the holes provided in the side wall of the beam 67 and lead out from the lower end of the beam 67. One end of the thermocouple element A 72 is connected to the bottom of the heat sink 62, and the other end is routed downward from the hole provided in the side wall of the beam 67 and lead out from the lower end of the beam 67. Each of the thermocouple elements A 71, 72 and the thermocouple element B 73 can also be connected to the bottom of the container holder 61 or the heat sink 62 by welding. Similarly, thermocouple elements A 76, 77 and a thermocouple element B 78 for measuring the temperature of the sample container assembly 202 are also connected to the bottom of the container holder 63 or the heat sink 64 by welding.

Note that both the sample container 69 and the container holder 61 of this embodiment are "sample containers" composing a device for thermal analysis of the claimed invention. The same applies to the sample container 70 and the container holder 63.

The container holder 61 is a circular holder for carrying the sample container 69 having a circular shape in plan view. The container holder 61 has a rather recessed part having a slightly larger diameter than the outer diameter of the sample container 69 and the sample container 69 can be fitted into the recessed part.

The heat sink 62 has a circular shape having almost the same diameter as the container holder 61. The heat sink 62 is desirably maintained at the same temperature as the internal temperature of the heating furnace 20 without being influenced by temperature change of the sample and the like. Therefore, the heat capacity of the heat sink 62 is preferably more than twice the sum of the heat capacities of the sample container 69 and the container holder 61.

The coupling member 65 is a member having a predetermined heat capacity and having a rod-like shape. In this embodiment, the material of the coupling member 65 can be for example platinum which is the material of the container holder 61. This thermal resistance of the coupling member 65 determines the thermal resistance R in Equation (3). The coupling member 65 is desirably placed coaxially with the center axis of the container holder 61 and the heat sink 62.

The beam 67 is a member having a rod-like external shape and having heat resistance. The beam 67 constitutes a three-hole insulating tube having three insulation holes. For the material of the beam 67, for example, alumina can be used. The beam 67 is disposed to extend in the vertical direction and allows the sample and the like to be placed on the differential balance 103 and allows thermocouple elements for measuring the temperature of the sample and the like to be routed.

The sample container 69 is a container for carrying a sample to be measured and is positioned by being fitted into the recessed part of the container holder 61. The material of the sample container 69 can be, for example, alumina considering the measurement temperature conditions and the like.

In this embodiment, for example, the material of the container holder 61, the heat sink 62, the coupling member 65, and the thermocouple element B 73 can be platinum (Pt) as described above, whereas the material of the thermocouple elements A 71, 72 can be a platinum rhodium alloy (PtRh). Using these materials as components, the connection between the thermocouple element A 71 and the thermocouple element A 72 forms a PtRh—Pt—PtRh joint. With this structure, the temperature difference between one PtRh—Pt joint and the other PtRh—Pt joint can be measured. This temperature difference is the temperature difference between the container holder 61 and the heat sink 62 of the sample container assembly 201.

Further, the temperature difference between one PtRh—Pt joint and the other PtRh—Pt joint in the above PtRh—Pt—PtRh joint can be measured as a voltage difference (VA−VB) between the thermocouple element A 71 and the thermocouple element A 72 as shown in FIG. 10(C).

In this embodiment, the sample container 69 is fitted into the recessed part of the container holder 61, so that the temperature difference between the sample container 69 and the heat sink 62 is considered to be approximate to the temperature difference between the container holder 61 and the heat sink 62, measured by the above PtRh—Pt—PtRh joint.

Further, in FIG. 10(C), the thermocouple element A 71 and the thermocouple element B 73 form a PtRh—Pt joint at a position of the container holder 61. Accordingly, the temperature of the container holder 61 can be determined by measuring the voltage difference (VA−VC) between the thermocouple element A 71 and the thermocouple element B 73. The temperature of the sample container 69 is considered to be approximate to the temperature of the container holder 61.

As in the sample container assemblies 101, 102, the container holders 61 and 63 are placed at axially symmetric positions with respect to the center axis of the heating furnace 20 in the sample container assemblies 201, 202. The heat sinks 62 and 64 can be similarly placed at axially symmetric positions with respect to the center axis of the heating furnace 20. The container holders 61 and 63 and the heat sinks 62 and 64 are all placed equidistant from the center axis of the heating furnace 20. Further, the sample containers 69, 70 are also placed at axially symmetric positions with respect to the center axis of the heating furnace 20.

The structure of the balance used in Embodiment 2 is identical to that of the balance 103 in Embodiment 1, so that further explanation is omitted here.

The structure of a temperature measurement unit used in Embodiment 2 is not different from that of the temperature measurement unit 300 used in Embodiment 1 except that the thermocouple elements A 71, 72, 76, 77 and the thermocouple elements B 73, 78 are connected instead of connecting the thermocouple elements A 31, 32, 36, 37 and the thermocouple elements B 33, 38, so that further explanation is omitted here.

Note that such variations of material choices as shown in FIGS. 6(A) to 6(d) can also be applied to the container holders 61, 63, the heat sinks 62, 64, the coupling members 65, 66, and the thermocouple elements A 71, 72, 76, 77 and the thermocouple elements B 73, 78 in this embodiment.

Further, the structure of the heating furnace 20 is also similar to that in Embodiment 1. The heat coil 21 is wound up and down for the same distance from the height of the bottom of the sample containers 69, 70 and the heat sinks 62, 64. Further, since the sample containers 69, 70 and the heat sinks 62, 64 are equidistant from the center axis of the heating furnace 20 in the radial direction, they are also equidistant from the cylindrical wall surface of the heating furnace 20. Therefore, the sample containers 69, 70 and the heat sinks 62, 64 are equally heated by the heating furnace 20.

As described above, according to this embodiment, the sample containers 69 and 70 are placed at symmetrical positions with respect to the center axis of the cylindrical heating furnace 20, and the heat sinks 62 and 64 are also placed at symmetrical positions with respect to the center axis of the heating furnace 20. The sample containers 69, 70 and the heat sinks 62, 64 are all placed equidistant from the center axis of the heating furnace 20. Further, the sample containers 69 and 70 are placed at the same height. The same applies to the heat sinks 62 and 64. With this structure, the sample containers 69, 70 and the heat sinks 62, 64 are equally heated in the heating furnace 20, so that in weight difference measurements, the effects of the buoyancy and convection flows can be surely cancelled and in addition, more accurate DSC measurement can be performed.

The present invention has been based on the drawings and the examples; however, it should be noted that those skilled in the art can easily make various alterations or modifications based on the present disclosure. Accordingly, it should be noted that those alterations or modifications are included in the scope of the present invention. For example, functions performed by the components or the process steps or the like can be rearranged in such a manner that does not cause any logical contradiction. For example, a plurality of components and steps can be combined or divided.

REFERENCE SIGNS LIST

1, 3: Container holder (Sample container)
2, 4: Heat sink
5, 6: Coupling member
7, 8: Beam
9, 10: Sample container
17: Comparator
18: Current driver
19: Furnace temperature sensor
20: Heating furnace (Heating unit)
21: Heat coil
22: Main shaft
24: Shutter
25: Light emitting device
26: Light receiving device
27: Driving coil
28: Magnet
31, 32: Thermocouple element A
31, 32: Thermocouple element B
40: Differential amplifier
41: Phase compensator
42: Current driver
50, 51, 52: Differential amplifier
61, 63: Container holder (Sample container)
62, 64: Heat sink
65, 66: Coupling member
67, 68: Beam
69, 70: Sample container
100, 500: Device for thermal analysis
101, 102, 201, 202: Sample container assembly
103: Balance (Weight measurement unit)
200: Balance control unit
300: Temperature measurement unit
400: Temperature control unit

The invention claimed is:

1. A device for thermal analysis comprising:
   a pair of sample container assembly sets including a first sample container assembly and a second sample container assembly, in each of which a sample container and a heat sink are connected using a member having a predetermined thermal resistance, wherein the heat sink has a heat capacity at least twice that of the sample container;
   a heating unit configured to equally heat the pair of sample container assembly sets, wherein the heating unit has a cylindrical shape, and wherein the sample containers and the heat sinks of the pair of sample container assembly sets are equidistant from a cylindrical wall surface of the heating unit;
   a temperature control unit configured to control the temperature of the heating unit;
   a weight measurement unit configured to measure the weight difference between a sample in the sample container of the first sample container assembly and a reference material in the sample container of the second sample container assembly; and
   a temperature measurement unit configured to measure the temperature difference between the temperature difference between the sample container and the heat sink of the first sample container assembly and the temperature difference between the sample container and the heat sink of the second sample container assembly;
   wherein the temperature control unit is adapted to change the temperature of the heating unit, and the weight measurement unit is adapted to measure the weight difference while the temperature of the heating unit is changed, and the temperature measurement unit is adapted to measure the temperature difference while the temperature of the heating unit is changed.

2. The device for thermal analysis according to claim 1, wherein the temperature measurement unit comprises:
   thermocouple elements made of first metal, connected to the sample containers and the heat sinks; and
   thermocouple elements made of second metal, connected to the sample containers,
   wherein the member having the thermal resistance is a member made of the second metal.

3. The device for thermal analysis according to claim 2, wherein the first metal is platinum, and the second metal is a platinum rhodium alloy.

4. The device for thermal analysis according to claim 2, wherein the first metal is a platinum rhodium alloy, and the second metal is platinum.

5. The device for thermal analysis according to claim 1, wherein the sample container of the first sample container assembly and the sample container of the second sample container assembly are placed at symmetrical positions with respect to the center axis of the cylindrical shape.

6. The device for thermal analysis according to claim 5, wherein the heating unit has a cylindrical shape, and the heat sink of the first sample container assembly and the heat sink of the second sample container assembly are placed at symmetrical positions with respect to the center axis of the cylindrical shape.

7. The device for thermal analysis according to claim 1, wherein the heat sinks are placed at the same height as the sample containers.

8. The device for thermal analysis according to claim 1, wherein the sample container of the first sample container assembly is placed coaxially with the center axis of the heat sink of the first sample container assembly, and the sample container of the second sample container assembly is placed coaxially with the center axis of the heat sink of the second sample container assembly.

9. The device for thermal analysis according to claim 1, wherein the weight measurement unit is a balance configured to measure the weight difference between the sample container assemblies.

10. A method for thermal analysis using a device for thermal analysis including:

a pair of sample container assembly sets including a first sample container assembly and a second sample container assembly, in each of which a sample container and a heat sink are connected using a member having a predetermined thermal resistance, wherein the heat sink has a heat capacity at least twice that of the sample container; and a heating unit configured to equally heat the first sample container assembly and the second sample container assembly, wherein the heating unit has a cylindrical shape, and wherein the sample containers and the heat sinks of the pair of sample container assembly sets are equidistant from a cylindrical wall surface of the heating unit, wherein the method comprises the steps of:

while changing the temperature of the heating unit, measuring the weight difference between a sample in the sample container of the first sample container assembly and a reference material in the sample container of the second sample container assembly; and at the same time as the measurement of the weight difference, measuring the temperature difference between the temperature difference between the sample container and the heat sink of the first sample container assembly and the temperature difference between the sample container and the heat sink of the second sample container assembly.

* * * * *